United States Patent [19]

Butter et al.

[11] 4,255,349

[45] Mar. 10, 1981

[54] CONVERSION OF SYNTHESIS GAS WITH IRON-CONTAINING CATALYST

[75] Inventors: Stephen A. Butter; Arthur W. Chester, both of Cherry Hill, N.J.

[73] Assignee: Mobil Oil Corporation, Fairfax, Va.

[21] Appl. No.: 970,307

[22] Filed: Dec. 18, 1978

[51] Int. Cl.³ .............................................. C07C 1/04
[52] U.S. Cl. ..................... 260/449.6 R; 260/449.6 M; 260/455 Z
[58] Field of Search ................. 260/449.6 R, 449.6 M, 260/449 R, 449 M

[56] References Cited

U.S. PATENT DOCUMENTS

| | | | |
|---|---|---|---|
| 3,553,104 | 1/1971 | Stover et al. | 208/120 |
| 4,086,262 | 4/1978 | Chang et al. | 260/449 R |

*Primary Examiner*—Howard T. Mars
*Attorney, Agent, or Firm*—Charles A. Huggett; Charles J. Speciale

[57] ABSTRACT

A method is disclosed for the conversion of synthesis gas to a liquid hydrocarbon product having a boiling range of less than 400° F. at a 90% overhead utilizing a novel catalyst prepared from a water-insoluble organic iron compound. The novel method involves contacting synthesis gas with a single particle catalyst containing iron, a crystalline acidic aluminosilicate zeolite having a silica-to-alumina ratio of at least 12, a pore size greater than about 5 Angstrom units, and a constraint index of about 1 to 12, and a matrix. The catalyst does not contain promoters.

8 Claims, No Drawings

CONVERSION OF SYNTHESIS GAS WITH IRON-CONTAINING CATALYST

CROSS REFERENCE TO RELATED CASES

This application is related to application Ser. No. 970,301, filed on even date herewith.

BACKGROUND OF THE INVENTION

1. Field of the Invention

This invention is concerned with an improved process for converting synthesis gas, i.e. mixtures of gaseous carbon oxides with hydrogen or hydrogen donors, to hydrocarbon mixtures.

Processes for the conversion of coal and other hydrocarbons, such as natural gas, to a gaseous mixture consisting essentially of hydrogen and carbon monoxide and/or dioxide are well known. Those of major importance depend either on the partial combustion of the fuel with an oxygen-containing gas or on the high temperature reaction of the fuel with steam, or on a combination of these two reactions. An excellent summary of the art of gas manufacture, including synthesis gas, from solid and liquid fuels is given in Encyclopedia of Chemical Technology, Edited by Kirk-Othmer, Second Edition, Volume 10, pages 353–433 (1966), Interscience Publishers, New York, New York.

It is also well known that synthesis gas will undergo conversion to reduction products of carbon monoxide, such as hydrocarbons, at from about 300° F. to about 850° F., under from about one to one thousand atmospheres pressure, over a fairly wide variety of catalysts. The Fischer-Tropsch process, for example, which has been most extensively studied, produces a range of liquid hydrocarbons, a portion of which have been used as low octane gasoline. Catalysts that have been studied for this and related processes include those based on iron, cobalt, nickel, ruthenium, thorium, rhodium and osmium, or their oxides.

Recently, it has been discovered that the conversion of synthesis gas into valuable products can be greatly enhanced by employing a special type of crystalline aluminosilicate zeolite exemplified by ZSM-5 in admixture with a carbon monoxide reduction catalyst. Thus, for example, in U.S. Pat. No. 4,086,262, there is disclosed a process for the conversion of syngas by passing the same at elevated temperature over a catalyst which comprises an intimate mixture of a Fischer-Tropsch component and a special type of zeolite such as ZSM-5. Said patent points out that the products produced are hydrocarbon mixtures which are useful in the manufacture of heating oil, high octane gasoline, aromatic compounds, and chemical intermediates.

Although U.S. Pat. No. 4,086,262 is primarily directed to multi-particle composite catalysts, i.e. the crystalline aluminosilicate component (one particle) is physically admixed with the Fischer-Tropsch component (another particle), nevertheless, Example 5 of said patent does disclose a single particle iron-containing catalyst (an alumina bound zeolite catalyst impregnated with iron).

As can well be appreciated, the patent and technical literature relating to the Fischer-Tropsch process, is, indeed, extensive and the various catalysts reported in the prior art have been used by themselves as well as in admixture with catalytically inactive supports such as kieselguhr. Although the reasons for using catalytically inactive supports have varied, nevertheless, it would appear that one reason for using the same was that it resulted in increased surface area of the Fischer-Tropsch component upon which it was deposited or admixed and that it also aided in controlling the heat requirements of the overall exothermic reactions.

It is also known in the art to admix a Fischer-Tropsch component with a material, such as silica-alumina which is known to be catalytically active for the conversion of hydrocarbons.

In copending application Ser. No. 970,301, filed on even date herewith, there is disclosed a syngas conversion process utilizing a single particle iron-containing catalyst prepared via impregnation techniques with a water-soluble iron salt. The instant application is directed towards the use of water-insoluble iron derivative of an organic such as iron oxalate to prepare single particle catalysts and the discovery that such catalysts are far more effective for the conversion of syngas than the corresponding catalysts made from water-soluble iron salts.

DESCRIPTION OF PREFERRED EMBODIMENTS

The novel process of this invention is directed towards an improvement in the process of converting syngas to a very specific product. The product with which the instant invention is concerned is a naphtha having a boiling range of less than 400° F. at a 90% overhead which is defined as a $C_5+$ naphtha wherein said fraction is at least 45 weight percent of the total hydrocarbons produced. The instant invention is also concerned with obtaining the above-defined product in good yields and good selectivities from the starting syngas material as well as towards the catalyst per se.

The novel process of this invention is carried out by contacting said synthesis gas with a catalyst which comprises at least three separate components which are present in a single particle as opposed to a mixture of three separate particles. The catalyst of this invention comprises iron, an acidic crystalline aluminosilicate zeolite having a pore size of about 5 Angstrom units, a silica alumina ratio of at least 12, and a constraint index of about 1–12 (preferably ZSM-5) and a matrix material. The crystalline aluminosilicates employed in the novel process of this invention are fully set forth in aforementioned U.S. Pat. No. 4,086,262 which is herein incorporated by reference. The preferred class of zeolites used is exemplified by ZSM-5, ZSM-11, ZSM-12, etc. As has heretofore been stated, the manner in which the iron is introduced into the catalyst is of prime importance.

The matrix portion of the single particle catalyst is not narrowly critical and suitable matrices include silica, alumina, silica-alumina, silica-zirconia, silica-magnesia, etc.

One surprising feature of the novel process of this invention is that the catalysts which are employed may be unpromoted and yet they still exhibit high activity with little evident aging, and, in fact, are capable of converting syngas to the olefinic or aromatic naphtha product previously described while producing no more than 30 weight percent of methane plus ethane, based on total hydrocarbons. In fact, the use of promoters, which the prior art found necessary in previous iron-containing catalysts, is definitely not preferred due to the fact that most promoters are alkaline in nature and they have a tendency to migrate to the acidic crystalline aluminosilicate zeolite component and to decrease the activity of the same. Therefore, it would appear that the single particle catalyst of the instant invention represents a significant departure from the teachings of the prior art in that not only are alkaline promoters not necessary for sustained operation, but, in fact, are detrimental to the activity of the zeolitic component.

The single particle iron-containing catalyst of this invention can be prepared by adding the appropriate acidic crystalline aluminosilicate previously defined and a water insoluble iron derivative of an organic iron to a hydrogel before drying, homogenizing the same, and thereafter forming either fixed bed or fluid catalysts by conventional techniques.

The water-insoluble derivatives of organic compounds include water-insoluble organic iron salts such as the oxalate, the formate, as well as mixtures thereof.

The amount of water-insoluble iron derivative of an organic compound which is added is not narrowly critical and an amount sufficient to produce 2.5 to 20 weight percent and more preferably 2.5 to 10 weight percent expressed as Fe, based on the finished catalyst, is used.

One embodiment of this invention resides in the in situ formation of the water insoluble organic iron derivative in the hydrogel. In this embodiment a water soluble iron salt such as iron sulfate or iron (II) gluconate is added to the hydrogel followed by treatment with oxalic or formic acid in order to form the organic salt in situ.

Following the addition of the water insoluble organic iron salt (either directly or prepared in situ), the catalyst can be formulated into a fixed bed or fluid catalyst by conventional techniques.

It is to be understood that methods of making fluidized catalysts containing crystalline aluminosilicate zeolites and matrices are well known in the art and that no novelty is claimed in this step per se. Thus, for example, a composite of the crystalline aluminosilicate zeolite and a siliceous matrix can be made by admixing an aqueous alkali metal silicate with or without a particulate weighting agent, such as kaolin clay, desirably as a dispersion in water so as to intimately mix the clay particles with the alkali metal silicate. This admixing is conveniently done at room temperature, although, of course, higher or lower temperatures may be employed if desired. The mixture is then heated, generally to a temperature of from 100°–160° F. and acid is added to adjust the pH to from about 8–10. The temperature is maintained for a time of about 1–6 hours or longer. At this point, if a silica-zirconia weighting agent (e.g. clay) matrix is desired, a zirconium salt is added, desirably as an aqueous solution thereof. Acid is then added to reduce the pH to about 4–7 and form a silica gel weighting agent or a silica gel-zirconia gel weighting agent slurry, which is then admixed with a slurry of the acidic crystalline aluminosilicate zeolite and the water insoluble organic iron salt previously described. The resulting composite is then homogenized and then treated with a source of ammonium ions or hydrogen ions in order to reduce the sodium content to a low level which is desirably less than about 0.1% sodium and then spray dried to produce fluid size particles.

As is generally known in fluid catalysts for catalytic cracking, the catalyst additionally includes a weighting agent. The most preferred weighting agent is kaolin clay. Other weighting agents may be substituted in whole or in part for the kaolin clay so long as the weighting agents are not detrimental to the finished catalyst.

The matrices may also be based on alumina for fluid catalysts, although such formulations generally do not lead to the desired physical characteristics. However, the use of an alumina matrix (or border) may be prepared for fixed bed catalysts.

The relative proportion of crystalline aluminosilicate zeolite to matrix is not narrowly critical and it can range from about 5–40 weight percent of the matrix.

As has been indicated earlier, the crystalline aluminosilicate zeolite, the iron compound and the matrix are then thoroughly mixed in a form of an aqueous slurry in order to homogenize the same and thereafter subdivided and dried to form the desired particles. A particularly good method of making microspherical particles (e.g. of particle size of about 1–200 microns) especially suitable for use in the fluidized process of this invention is spray-drying.

The temperature of the air (or other gas) entering the spray drier is ordinarily within the range of 500°–1,000° F. The temperature used will depend on such factors as the quantity of material to be dried and the quality of air used in the drying. The evaporation rate will vary depending on the quantity of air used in the drying. The temperature of the particles which are being dried is generally within the range of 150°–400° F. at the completion of the drying, but preferably 200°–350° F.

The drying may be affected by a process in which the particles to be dried and a hot air stream are moving in the same direction for the entire drying period (concurrent drying) or where the hot stream flows in the opposite direction (countercurrent drying), or by semi-concurrent drying. It is to be understood that spray-drying to form fluidized catalysts is well known in the art and a representative procedure is described in U.S. Pat. No. 3,553,104, the entire contents of which are incorporated by reference.

The iron-containing catalysts are thereafter heated in order to decompose the organic iron compounds. The temperature utilized is not critical and it can range from 115° F. to 1200° F. for periods of time ranging from about 1 to 48 hours.

The iron-containing catalysts must be then pretreated prior to use for the conversion of syngas. In this connection, it has been found that the nature of the pretreatment is critical. The catalyst must be pretreated with syngas or with CO prior to use. As opposed to prior art catalysts, the use of hydrogen alone has an adverse effect on catalytic properties. Treatment with syngas or carbon monoxide is conveniently carried out at atmospheric pressure and at temperatures of about 550°–650° F. for periods of time ranging from about ½ hour up to about 24 hours.

Another embodiment of this invention resides in a modification involving the in situ formation of the water insoluble organic iron salt. In this embodiment, a water-soluble iron salt such as ferrous sulfate or iron gluconate is added to an alumina dispersion followed by addition of an appropriate organic acid such as oxalic acid in order to form an alumina-iron oxalate composition. This composition can be used as the source of iron by the addition of the same to the hydrogel-containing matrix and crystalline aluminosilicate zeolite followed by processing in the manner previously described.

A particularly desirable embodiment of this invention resides in the use of matrices made from mixtures of colloidal silica and colloidal alumina instead of conventional procedures in which sodium silicate and aluminum sulfate are employed. In this embodiment colloidal alumina is added to colloidal silica which usually contains a slurry of a weighting agent such as clay. Crystalline aluminosilicate zeolite and water-insoluble organic iron salt are added followed by homogenizing and drying in the manner previously described.

The acidic crystalline aluminosilicate component of the catalyst is characterized by a pore dimension greater than about 5 Angstroms, i.e. it is capable of sorbing paraffins, and it has a silica-to-alumina ratio of at least 12 and a constraint index within the range of 1 to 12. Zeolite A, for example, with a silica-to-alumina ratio of 2.0 is not useful in this invention, and it has no pore dimension greater than about 5 Angstroms.

The crystalline aluminosilicates herein referred to, also known as zeolites, constitute an unusual class of natural and synthetic minerals. They are characterized by having a rigid crystalline framework structure composed of an assembly of silicon and aluminum atoms, each surrounded by a tetrahedron of shared oxygen atoms, and a precisely defined pore structure. Exchangeable cations are present in the pores.

The acidic crystalline aluminosilicate component preferably is in the hydrogen form.

The catalysts referred to herein utilize members of a special class of zeolites exhibiting some unusual properties. They are very active even with silica-to-alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in this invention comprise, in combination: a silica-to-alumina ratio of at least about 12; and a structure providing constrained access to the crystalline free space.

The silica-to-alumina ratio referred to may be determined by conventional analysis. This ratio is meant to represent as closely as possible, the ratio in the rigid anionic framework of the zeolite crystal and to exclude aluminum in the binder or in cationic or other form within the channels. Although zeolites with a silica-to-alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the and the zeolite is not of the desired type. Zeolites with windows of 10-membered rings are preferred, although excessive puckering or pore blockage may render these zeolites substantially ineffective. Zeolites with windows of 12-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1,000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e. 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those which employ a zeolite having a constraint index from 1.0 to 12.0. Constraint Index (CI) values for some typical zeolites including some not within the scope of this invention are:

| CAS | C.I. |
|---|---|
| Erionite | 38 |
| ZSM-5 | 8.3 |
| ZSM-11 | 8.7 |
| ZSM-35 | 6.0 |
| TMA Offretite | 3.7 |
| ZSM-38 | 2.0 |
| ZSM-12 | 2 |
| Beta | 0.6 |
| ZSM-4 | 0.5 |
| Acid Mordenite | 0.5 |
| REY | 0.4 |
| Amorphous | |

| CAS | C.I. |
| --- | --- |
| silica-alumina | 0.6 |

The above-described Constraint Index is an important and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint index seems to vary somewhat with severity of operation (conversion). Therefore, it will be appreciated that it may be possible to so select test conditions to establish multiple constraint indexes for a particular given zeolite which may be both inside and outside the above-defined range of 1 to 12.

Thus, it should be understood that the parameter and property "Constraint Index" as such value is used herein as an inclusive rather than exclusive value. That is, a zeolite when tested by any combination of conditions within the testing definition set forth hereinabove to have a constraint index of 1 to 12 is intended to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-35 and ZSM-38, and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-35 is described in U.S. Pat. No. 4,016,245 and ZSM-38 is described in U.S. Pat. No. 4,046,859, both of which are incorporated herein by reference.

The novel process of this invention is carried out at temperatures ranging from about 500°–600° F. and more preferably from 550° to about 580° F. The novel process of this invention is carried out at gas hourly space velocities (GHSV), ranging from 400 to 20,000 and more desirably from 500 to 6,000, based on fresh feed and total catalyst volume. Hydrogen to carbon oxides ratios can vary from 0.5:1 to 2:1 and more preferably are about 1:1, pressures ranging from 50 to 1,000 psig and more preferably from 150 to 400 psig are employed.

It is to be understood that although this invention has been described with reference to iron only, the catalyst can contain minor amounts of additional substances such as tin, phosphorus and tungsten, rare earth, vanadium, manganese, molybdenum, etc.

The following examples will illustrate the novel process of this invention.

EXAMPLE 1

The fluid catalyst matrix of this example was prepared in the following manner. Q-Brand silicate solution (7972.2 grams) was added to a water slurry containing 1861 grams WP kaolin clay in 83.7 lbs of water. After heating to 120° F., 752.4 grams of 97% $H_2SO_4$ was added and the resulting hydrogel heated to 140° F. for two hours. A solution containing 139.4 grams aluminum sulfate in 560 cc water was added, followed by 166.7 grams sodium zirconium silicate solution. The mixture was acidified with $H_2SO_4$ to a pH of 4.7 and left to stand overnight to form a gel.

EXAMPLE 2

300 grams of the gel prepared in Example 1 was mixed with 14.1 grams of the ammonium form of ZSM-5 and 14.7 grams of ferrous oxalate dihydrate. After blending well, the mixture was dried in vacuo, exchanged two times with 69 grams $(NH_4)_2SO_4$ in 462 cc $H_2O$, washed to remove sodium and sulfate and oven dried. One half of the dried material was calcined in air for three hours at 1000° F. The finished catalyst contained 7.7% iron and 0.02% sodium.

EXAMPLE 3

The other half of the catalyst prepared in Example 2 was treated in nitrogen for three hours at 1000° F. The iron content was 7.7%.

EXAMPLE 4

One hundred grams of the gel prepared in Example 1 was mixed with 7.5 grams ferrous sulfate 7-hydrate in 30 cc of water, followed by the addition of 5.0 grams oxalic acid dihydrate dissolved in 40 cc of water. To this mixture was added 4.7 grams of ammonium ZSM-5 zeolite, and after homogenization and drying in vacuo, the catalyst was exchanged twice with 23 grams of ammonium sulfate in 155 cc $H_2O$, and washed until free of sulfate ion. After drying at ca. 115° F., the finished catalyst contained 7.8% iron.

EXAMPLE 5

The procedure used in Example 4 was repeated with the exception that sufficient ferrous sulfate heptahydrate was used to give a finished catalyst containing 13.1% iron.

EXAMPLE 6

The procedure of Example 4 was repeated with the exception that sufficient iron sulfate heptahydrate was used to give 16.1% iron in the finished catalyst.

EXAMPLE 7

Q-brand silicate solution (7972.2 grams) was added to a water slurry containing 1861 grams WP kaolin clay in 83.7 lbs of water. After heating to 120° F., 752.4 grams of 97% $H_2SO_4$ was added and the resulting hydrogel heated to 140° F. for two hours. A solution containing 139.4 grams aluminum sulfate in 560 cc water was added, followed by 166.7 grams sodium zirconium silicate solution. The mixture was acidified with $H_2SO_4$ to a pH of 4.7 and left to stand overnight. After removal of 2000 grams of the gel for other studies, 2563 grams of the ammonium form of ZSM-5 slurried with 8000 cc $H_2O$ was added to the remainder of the gel, and the mixture homogenized and spray-dried. The gel was exchanged twice with 6 lbs of ammonium sulfate in 40 lbs $H_2O$ and washed until free of sulfate, followed by drying at 250° F. The Na content was less than 0.01%. 10.0 grams of the above was impregnated with a solution containing 6.70 grams of ferric oxalate, $Fe_2(C_2O_4)_3 \cdot 6H_2O$ in 60 cc of water. After drying in vacuo and calcining in air for three hours at 1000° F., the finished catalyst contained 8.5% iron (Ex. 7a). (A portion of this catalyst was maintained in the uncalcined state, labeled 7b.)

It is to be noted that ferric oxalate is water-soluble so that this example is outside the scope of the instant invention.

EXAMPLE 8

A fluid catalyst matrix was prepared by adding 10,722 grams Q-Brand sodium silicate to a slurry of 930 grams kaolin clay in 112.5 lbs $H_2O$. After heating to 120° F., 1012 grams of 97% $H_2SO_4$ was added. At pH 10.51 the gel was heated to 140° F. for two hours and a solution of 186.6 grams aluminum sulfate in 746 cc $H_2O$ was added, followed by 166.7 grams of sodium zirconium silicate in 1617 cc $H_2O$. The pH was adjusted to 4.58 by addition of $H_2SO_4$ and left to stand overnight.

EXAMPLE 9

The catalyst of this example was prepared by filtering one-half of the gel matrix prepared in Example 8. The filter cake was slurried with 300 grams $(NH_4)_2SO_4$ in 6 liters of water, filtered again, and washed with water until the washings were free of sulfate. The gel was homogenized with the addition of 1132 grams of low sodium ZSM-5 zeolite (30.6% solid content) in 3400 cc $H_2O$ and 1204 grams ferrous oxalate dihydrate, and the mixture spray dried. An air calcination for 3 hours at 1000° F. gave the finished catalyst which contained 9.9% iron. Other properties are listed below:

| PROPERTIES OF IRON/ZSM-5 FLUID SYN GAS CATALYSTS | |
|---|---|
| Composition, Wt. % | |
| $SiO_2$ | 73.8 |
| $Al_2O_3$ | 6.1 |
| $Fe_2O_3$ (fe) | 14.2 (9.9) |
| $ZrO_2$ | ~1.5 |
| HZSM-5 | ~30 |
| $SiO_2/Al_2O_3$ (zeolite) | 70/1 |
| Surface Area, $m^2/g$ | 287 |
| Particle Density, g/cc | .575 |
| Real Density, g/cc | 2.65 |
| Packed Density, g/cc | 0.35 |
| Pore Volume, cc/g | 0.91 |

| PARTICLE SIZE DISTRIBUTION | |
|---|---|
| Microns | Calculated Wt % |
| 0–20 | 2.2 |
| 0–30 | 4.3 |
| 0–40 | 9.1 |
| 0–60 | 28.8 |
| 0–80 | 56.4 |
| 0–100 | 79.3 |
| Mean Diameter | 75.6 microns |

EXAMPLE 10

One hundred grams of the fluid matrix prepared in Example 9 was mixed with 8.65 grams ferrous sulfate.7-$H_2O$ and 1.00 grams copper sulfate in 100 cc $H_2O$. Oxalic acid dihydrate (11.5 grams) in 100 cc of water was added followed by 4.7 grams of low sodium form ZSM-5 (11% dry solids). The mixture was homogenized, dried, and washed until sulfate-free. After drying and calcining at 1000° F. for 3 hours, the finished catalyst contained 8.6% iron and 2.7% copper.

EXAMPLE 11

The procedure of Example 10 was followed with the exception that the $CuSO_4$ was replaced with 2.54 grams $Cr_2(SO_4)_3$. The finished catalyst contained 11.6% iron and 0.15% chromium after calcination.

EXAMPLE 12

One hundred grams of the fluid gel matrix prepared in Example 9 was exchanged with ammonium sulfate and washed with water until sulfate-free. A solution containing 12.9 grams iron (11) gluconate in 200 cc was added, followed by 5.3 grams oxalic acid dihydrate in 40 cc $H_2O$ and 9.79 grams low sodium ZSM-5. The mixture was homogenized, filtered, dried and calcined at 1000° F. for 3 hours giving a finished catalyst with 5.7% iron content.

EXAMPLE 13

A fluid catalyst gel matrix for this example was prepared by adding 10,722 grams Q-Brand sodium silicate to a slurry containing 930 grams of WP kaolin clay in 112.5 lbs $H_2O$. The procedure of Example 8 was followed identically. The next day the gel was divided into three equal portions.

EXAMPLE 14

A one-third portion of the gel prepared in Example 13 was filtered, and the filter cake was slurried with a solution containing 1364 grams $FeSO_4.7H_2O$ in 5400 cc water, followed by the addition of 682 grams oxalic acid dihydrate in 6300 cc $H_2O$. After filtration, the gel was slurried with 300 ppm ammonium sulfate dissolved in 6 liters of water, refiltered and washed with water until the washings were sulfate-free. A slurry containing 755 grams of acid ZSM-5 (30.6% solids) in 3750 cc $H_2O$ was added and the mixture was homogenized and spray-dried. The finished catalyst after calcination in air at 1000° F. for 3 hours contained 12.7% iron. Other properties are listed in the following table

| TABLE | |
|---|---|
| Zeolite/iron wt ratio = 0.92 | |
| Surface area | 358 $m^2/g$ |
| Density, real | 2.55 g/cc |
| Density, particle | 1.30 g/cc |
| Density, packed | 0.37 g/cc |
| Powder pore volume | 0.36 cc/g |
| Particle size, microns | Wt % |
| 0–20 | 1.7 |
| 0–30 | 8.9 |
| 0–40 | 20.3 |
| 0–60 | 43.6 |
| 0–80 | 60.8 |
| 0–100 | 72.3 |
| Mean particle diameter | 64.0 microns |

EXAMPLE 15

The catalyst of this example was prepared by contacting one-third of the gel prepared in Example 13 with a solution containing 300 grams ammonium sulfate in 6 liters $H_2O$ for one hour. The gel was then filtered and washed with water until the washings appeared sulfate-free. A solution containing 2783 grams of $FeSO_4.7H_2O$ in 10.8 liters $H_2O$ was slurried with the gel cake and the mixture heated to 120° F., after which a hot (~150° F.) solution containing 1391 grams $H_2C_2O_4.2H_2O$ in 10 liters $H_2O$ was added. After filtration and water washing to remove sulfate ions, the gel cake was mixed with 1270 grams acid ZSM-5 (30.6% solids) in 6780 cc $H_2O$, homogenized, and spray-dried. The finished catalyst was calcined in air at 1000° F. for three hours and contained 23.8% iron. Other properties are shown in the following table:

TABLE

| Zeolite/iron wt ratio = 0.67 | |
|---|---|
| Surface area, m²g | 267 |
| Density, real, g/cc | 2.90 |
| Density, particle, g/cc | 1.68 |
| Density, packed, g/cc | 0.36 |
| Particle microns | Wt % |
| 0–20 | 17.6 |
| 0–30 | 26.9 |
| 0–40 | 37.1 |
| 0–60 | 56.6 |
| 0–80 | 72.0 |
| 0–100 | 82.6 |
| Mean particle diameter | 50.5 microns |

EXAMPLE 16

A pure silica-base catalyst was prepared by mixing 37.0 grams of an aqueous silica gel (sold as Ludox-LS ® by E. I. du Pont de Nemours & Co.) with 7.0 grams ferrous oxalate dihydrate and 1.4 grams of ZSM-5 in the ammonium form. After homogenizing and drying, the finished catalyst contained 10.5% iron.

EXAMPLE 17

A clay-free silica gel matrix with small amounts of zirconia and alumina added to enhance physical properties was prepared by adding 205 cc of 97% $H_2SO_4$ to a warm (120° F.) solution containing 3986 grams Q-brand sodium silicate in 41.85 lbs of deionized water. The gel after heating to 140° F. for two hours and cooled was mixed with 70 grams aluminum sulfate in 280 cc $H_2O$, followed by 83 grams of sodium zirconium silicate in 805 cc $H_2O$, which was acidified with 55 cc of sulfuric acid. The pH was adjusted to 4.68 by addition of 20% $H_2SO_4$ solution and stirred gently over ca. 65 hours.

EXAMPLE 18

This catalyst was prepared by adding a solution containing 11.5 grams of $FeSO_4.7H_2O$ in 45 cc $H_2O$ to 137.1 grams of the gel prepared in Example 17 which contained 8.97% solids on a dry basis. A solution of 7.7 grams oxalic acid dihydrate in 65 cc $H_2O$ was then added to the gel, followed by 4.6 grams of ZSM-5 in the ammonium form. After homogenizing and drying, the catalyst was contacted twice with a solution containing 46 grams ammonium sulfate in 300 cc water and finally washed until sulfate-free. The dry, finished catalyst contained 11.1% iron.

EXAMPLE 19

This catalyst was prepared in a manner identical to that in Example 18 except one-half the amount of zeolite was used. The finished catalyst contained 11.9% iron.

EXAMPLE 20

This example illustrates the use of pure alumina as a binder for the metal and zeolite components. The catalyst was prepared by blending together 7.0 grams $FeC_2O_4.2H_2O$, 4.4 grams ammonium ZSM-5, and 11.7 grams α-alumina monohydrate. The catalyst contained 9.1% iron in finished form.

EXAMPLE 21

This catalyst was prepared by blending 4.4 grams ammonium ZSM-5 and 11.7 grams alpha-alumina monohydrate and impregnating the mixture with 15.72 grams $Fe(NO_3)_3.9H_2O$ dissolved in 17 cc $H_2O$. After drying, the calcined catalyst (1000° F. for 3 hours) contained 7.5% iron.

This catalyst was prepared by impregnating as is outside the scope of this invention.

EXAMPLE 22

Another pure alumina supported catalyst was prepared by adding 40.8 grams Q-Loid ® A-30 alumina dispersion (24.77% solids) to a solution of 12.9 grams iron (11) gluconate in 75 cc $H_2O$ at 140° F. A solution containing 5.2 grams oxalic acid dihydrate in 45 cc $H_2O$ was then added, followed by 9.79 grams of low sodium ZSM-5 (30.6% solids). The finished catalyst, dried and calcined at 1000° F. for three hours, contained 4.25% iron.

Example 23 is illustrative of catalysts prepared by combining highly dispersed silica and alumina fluid matrices. This example incorporates the metal and ZSM-5 class zeolite in a matrix prepared by mixing colloidal dispersions of silica and alumina and shows improved physical properties and higher activity and selectivity for the mixed sol matrix.

EXAMPLE 23

The mixed silica-alumina sol catalyst was prepared by adding 2000 grams Ludox-LS ® silica sol in 1535 cc of water to a clay dispersion containing 348.8 grams WP kaolin in 4667 cc $H_2O$. An alumina dispersion prepared by the addition of 666.7 grams Dispal-M ® alumina to 40 grams of 70% nitric acid + 6040 cc water was then added to the above-prepared silica-clay mixture, followed by 3268 grams of the low sodium form of ZSM-5 in 2488 cc $H_2O$. Finally, a slurry containing 1049 grams ferrous oxalate dihydrate in 2489 cc $H_2O$ was added and the mixture was then homogenized and spray-dried. The fluid catalyst was heated in nitrogen at ca. 1100° F. for three hours followed by a final air calcination for three hours at 1000° F. The finished catalyst contained 9.1% iron. Other properties are listed below:

TABLE

| Composition, wt % | |
|---|---|
| $SiO_2$ | 21 |
| $Al_2O_3$ | 21 |
| Clay | 11 |
| HZSM-5 | 34 |
| $Fe_2O_3$ | 13 |
| Real density, g/cc | 2.72 |
| Packed density, g/cc | 0.50 |
| Pore volume, cc/g | 0.48 |
| Zeolite/iron wt ratio | 3.8 |
| Particle size, microns | Wt % |
| 0–20 | 0.6 |
| 0–30 | 9.6 |
| 0–40 | 28.2 |
| 0–60 | 61.1 |
| 0–80 | 78.1 |
| 0–100 | 86.2 |
| Mean particle diameter | 53.0 microns |

(Examples 24 through 27 illustrate the use of fluid silica-alumina of different ratios and optionally a clay weighting agent as catalyst matrices.)

EXAMPLE 24

A gel matrix with a $SiO_2/Al_2O_3$/clay ratio of 60:20:20 was prepared by adding 8333 grams Q-brand sodium silicate to a slurry of 930 grams WP kaolin clay in 87.4 lbs of water. After heating to 120° F. 786.5 grams of 70% $H_2SO_4$ was added. After one hour at 120° F. a solution containing 4665 grams aluminum sulfate in 18,659 cc $H_2O$ was added and the gel stirred overnight at pH 4.5. The gel was then filtered and washed with 4 volumes of 5% $(NH_4)_2SO_4$ solution, followed by water until the washings were free of sulfate. One third of the gel matrix which contained 10.92% solids was mixed with 1177 grams $FeC_2O_4.2H_2O + 4000$ cc $H_2O$ and 3409 grams low sodium ZSM-5 (30.6% solids) + 2000 cc $H_2O$, and the mixture was homogenized and spray-dried. The calcined (1000° F./3 hr) catalyst contained 11.9% iron. Other properties are listed in the following Table.

TABLE

| Pore volume, cc/g | 0.76 |
|---|---|
| Packed density, g/cc | 0.31 |
| Real density, g/cc | 2.52 |
| Particle density, g/cc | 1.3 |
| Surface area, m²/g | 399 |
| Particle size, microns | Wt % |
| 0–20 | 3.3 |
| 0–30 | 5.3 |
| 0–40 | 9.7 |
| 0–60 | 26.6 |
| 0–80 | 50.5 |
| 0–100 | 72.6 |
| Mean particle diameter | 80.7 microns |

EXAMPLE 25

A gel with a $SiO_2/Al_2O_3$/clay ratio of 69.75:5.25:25 was prepared in the manner of Example 24. After washing, 72.8 grams of the gel containing 13.88% solids was homogenized with 7.7 grams $FeSO_4.7H_2O$ in 30 cc $H_2O$, 5.2 grams $H_2C_2O_4.2H_2O$ in 35 cc $H_2O$, and 3.0 grams ammonium ZSM-5. The dried catalyst was exchanged twice with 23 grams $(NH_4)_2SO_4$ in 150 cc $H_2O$ and washed until sulfate-free. The dried, finished catalyst contained 5.0% iron.

EXAMPLE 26

In this example a spray-dried catalyst with a $SiO_2/Al_2O_3$ ratio (clay-free) of 87:13 was prepared by co-gelling sodium silicate and aluminum sulfate and adding 40 wt% HZSM-5. Ten grams of the ammonium sulfate exchanged, washed and calcined (900° F.) catalyst was then impregnated with 12.5 grams $Fe(NO_3)_3.9H_2O$ in 6 cc $H_2O$ and dried. After calcining for 3 hours at 1000° F., the finished catalyst contained approximately 13% iron.

EXAMPLE 27

This example illustrates a ferric nitrate impregnated version of a mixed $SiO_2.Al_2O_3$ sol catalyst for comparison with Example 23.

A spray-dried $SiO_2.Al_2O_3$.clay matrix was prepared in a manner similar to that of Example 23 with the exception that ferrous oxalate was not added. The matrix properties was shown in the following Table.

TABLE

| Matrix composition, wt % | |
|---|---|
| $SiO_2$ | 29 |
| $Al_2O_3$ | 24 |
| Clay | 12 |
| HZSM-5 | 40 |
| Pore volume, cc/g | 0.58 |
| Packed density, g/cc | 0.53 |
| Particle size, microns | Wt % |
| 0–20 | 13.1 |
| 0–30 | 26.8 |
| 0–40 | 40.0 |
| 0–60 | 60.6 |
| 0–80 | 74.1 |
| 0–100 | 82.7 |
| Mean particle diameter | 71.2 microns |

Fifteen grams of this matrix was impregnated with 15.2 gm $Fe(NO_3)_3.9H_2O$ dissolved in 9 cc deionized water. After drying and calcining for 3 hours at 1000° F. in air, the finished catalyst contained 10.7% iron.

The catalysts were evaluated for the conversion of syngas to gasoline at 200 psig and a 1:1 $CO/H_2$ ratio. The following table gives the results obtained during the second day (except as noted) of the evaluation after the catalysts had been conditioned in $CO/H_2$ for the times and temperatures listed in the table.

| EXAMPLE | 2 | 3 | 4 |
|---|---|---|---|
|  | | day 1 | |
| Run Time, Hours | 42 | 18 | 18 |
| GHSV | 591 | 604 | 627 |
| WHSV | 0.94 | 0.98 | 0.92 |
| Temp., °F., Average | 556 | 562 | 550 |
| Hot Spot | 574 | 574 | 568 |
| CO Conversion, wt % | 51.4 | 48.6 | 83.9 |
| $H_2$ Conversion, wt % | 55.9 | 54.7 | 68.1 |
| % wt C Converted to: | | | |
| Hydrocarbon | 66.9 | 67.5 | 57.3 |
| Product Yield, wt % | | | |
| HC | 16.4 | 14.2 | 23.4 |
| $H_2O$ | 16.7 | 12.0 | 7.4 |
| $H_2$ | 3.3 | 3.6 | 2.5 |
| CO | 44.9 | 47.3 | 14.9 |
| $CO_2$ | 24.7 | 22.9 | 51.9 |
| Hydrocarbon Composition, wt % | | | |
| $C_1$ | 21.8 | 22.0 | 20.3 |
| $C_2$ | 7.2 | 5.4 | 11.3 |
| $C_3$ | 4.8 | 7.8 | 5.6 |
| $C_4$ | 10.7 | 14.5 | 7.2 |
| $C_5$ | 9.4 | 7.4 | 7.5 |
| $C_6+$ | 55.5 | 43.0 | 48.1 |
| Olefins, wt % by C No. | | | |
| $C_2=$ | 14.8 | 23.8 | 5.3 |
| $C_3=$ | 5.6 | ~0 | 0.2 |
| $C_4=$ | 9.3 | 1.0 | 21.3 |
| $C_5=$ | 11.9 | 10.9 | 38.8 |
| $C_5$ Olefin Distribution, wt % | | | |
| $C_5=1$ | 1.6 | 1.7 | 1.8 |
| $2M1C_4=$ | 14.7 | 13.8 | 16.1 |
| $3M1C_4=$ | 1.1 | 0.9 | 1.2 |
| $T2C_5=$ | 12.5 | 12.9 | 11.3 |
| $C_2C_5=$ | 4.9 | 5.2 | 5.3 |
| $2M2C_4=$ | 65.2 | 65.5 | 64.5 |
| $C_6+$ Aromatics, wt % | 21.2 | 19.9 | 12.2 |
| Liq. Prod. 90% Pt., °F. (D-2887) | 360 | 387 | 383 |
| Conditioned in 1:1 $CO/H_2$, °F./hr | 600/65 | 600/65 | 618/16 |

| EXAMPLE | 5 | 6 | 7a |
|---|---|---|---|
| Run Time, Hours | 18 | 42 | 18 |
| GHSV | 708 | 741 | 994 |
| WHSV | 0.97 | 0.94 | 1.02 |
| Temp., °F., Average | 537 | 537 | 546 |
| Hot Spot | 565 | 565 | 566 |
| CO Conversion, wt % | 90.5 | 86.3 | 49.4 |
| $H_2$ Conversion, wt % | 71.4 | 70.7 | 56.3 |
| % wt C Converted to: | 56.8 | 58.0 | 60.1 |
| Hydrocarbon | | | |
| Product Yield, wt % | | | |
| HC | 25.7 | 25.4 | 14.9 |
| $H_2O$ | 6.6 | 7.3 | 6.3 |
| $H_2$ | 2.2 | 2.3 | 3.2 |
| CO | 8.8 | 12.6 | 46.8 |
| $CO_2$ | 56.6 | 52.4 | 28.7 |
| Hydrocarbon Composition, wt % | | | |
| $C_1$ | 19.1 | 16.3 | 20.4 |
| $C_2$ | 11.1 | 10.3 | 13.2 |
| $C_3$ | 5.3 | 5.9 | 19.3 |

-continued

| | | | |
|---|---|---|---|
| $C_4$ | 7.0 | 7.1 | 13.5 |
| $C_5$ | 8.6 | 10.6 | 3.8 |
| $C_6+$ | 48.9 | 49.9 | 29.8 |
| Olefins, wt % by C No. | | | |
| $C_2=$ | 3.1 | 9.4 | 24.1 |
| $C_3=$ | 12.2 | 21.3 | 59.2 |
| $C_4=$ | 33.6 | 56.8 | 71.5 |
| $C_5=$ | 47.2 | 72.0 | 89.0 |
| $C_5$ Olefin Distribution, wt % | | | |
| $C_5=1$ | 1.6 | 1.8 | 4.6 |
| $2M1C_4=$ | 16.9 | 16.0 | 9.8 |
| $3M1C_4=$ | 1.3 | 1.3 | 0.7 |
| $T2C_5=$ | 10.9 | 11.9 | 28.1 |
| $C_2C_5=$ | 5.3 | 5.8 | 14.0 |
| $2M2C_4=$ | 64.0 | 63.1 | 42.8 |
| $C_6+$ Aromatics, wt % | 5.9 | 0.4 | 0.4 |
| Liq. Prod. 90% Pt., °F. (D-2887) | 391 | 396 | 354 |
| Conditioned in 1:1 $CO/H_2$, °F./hr | 616/18.5 | 615/18.5 | 609/17 |

| EXAMPLE | 7b | 9 | 10 |
|---|---|---|---|
| Run Time, Hours | 18 | 18 | 18 |
| GHSV | 670 | 583 | 477 |
| WHSV | 1.02 | 1.13 | 1.07 |
| Temp., °F. Average | 555 | 563 | 555 |
| Hot Spot | 567 | 574 | 568 |
| CO Conversion, wt % | 47.2 | 71.0 | 75.4 |
| $H_2$ Conversion, wt % | 54.0 | 62.5 | 65.3 |
| % wt C Converted to: | | | |
| Hydrocarbon | 66.9 | 59.6 | 58.1 |
| Product Yield, wt % | | | |
| HC | 14.8 | 20.5 | 21.2 |
| $H_2O$ | 10.0 | 7.8 | 7.3 |
| $H_2$ | 3.3 | 2.7 | 2.5 |
| CO | 49.1 | 27.0 | 22.8 |
| $CO_2$ | 22.8 | 42.0 | 46.2 |
| Hydrocarbon Composition, wt % | | | |
| $C_1$ | 20.7 | 18.8 | 21.3 |
| $C_2$ | 10.1 | 8.5 | 13.9 |
| $C_3$ | 4.3 | 5.7 | 5.8 |
| $C_4$ | 9.6 | 9.9 | 8.1 |
| $C_5$ | 8.0 | 7.6 | 7.7 |
| $C_6+$ | 47.4 | 49.6 | 43.2 |
| Olefins, wt % by C No. | | | |
| $C_2=$ | 15.3 | 10.6 | 5.9 |
| $C_3=$ | 20.4 | 3.6 | 3.1 |
| $C_4=$ | 25.0 | 17.4 | 29.5 |
| $C_5=$ | 30.8 | 25.1 | 46.9 |
| $C_5$ Olefin Distribution, wt % | | | |
| $C_5=1$ | 1.1 | 1.8 | 1.3 |
| $2M1C_4=$ | 12.9 | 14.4 | 13.7 |
| $3M1C_4=$ | 0.8 | 1.0 | 1.0 |
| $T2C_5=$ | 11.6 | 12.8 | 11.0 |
| $C_2C_5=$ | 5.0 | 5.9 | 5.0 |
| $2M2C_4=$ | 68.6 | 64.1 | 67.9 |
| $C_6+$ Aromatics, wt % | 14.8 | 18.1 | 8.5 |
| Liq. Prod. 90% Pt., °F. (D-2887) | 340 | 379 | 351 |
| Conditioned in 1:1 $CO/H_2$, °F./hr | 609/17 | 610/17 | 600/17 |

| EXAMPLE | 11 | 12 | 14 |
|---|---|---|---|
| Run Time, Hours | 18 | 18 | 18 |
| GHSV | 563 | 612 | 661 |
| WHSV | 1.21 | 0.96 | 0.97 |
| Temp., °F., Average | 542 | 556 | 556 |
| Hot Spot | 568 | 571 | 570 |
| CO Conversion, wt % | 79.15 | 61.6 | 74.5 |
| $H_2$ Conversion, wt % | 67.25 | 66.1 | 68.9 |
| % wt C Converted to: | | | |
| Hydrocarbon | 58.0 | 61.2 | 57.5 |
| Product Yield, wt % | | | |
| HC | 21.4 | 18.2 | 20.9 |
| $H_2O$ | 8.3 | 9.1 | 7.3 |
| $H_2$ | 2.3 | 2.7 | 2.5 |
| CO | 19.4 | 35.4 | 23.5 |
| $CO_2$ | 48.6 | 34.5 | 45.8 |
| Hydrocarbon Composition, wt % | | | |
| $C_1$ | 17.9 | 16.8 | 17.8 |
| $C_2$ | 11.2 | 6.6 | 9.5 |
| $C_3$ | 6.9 | 3.6 | 4.4 |
| $C_4$ | 5.7 | 9.1 | 8.2 |
| $C_5$ | 7.2 | 9.7 | 9.3 |
| $C_6+$ | 51.2 | 54.1 | 50.7 |

-continued

| | | | |
|---|---|---|---|
| Olefins, wt % by C No. | | | |
| $C_2=$ | 9.1 | 21.8 | 16.6 |
| $C_3=$ | 49.2 | 20.3 | 16.1 |
| $C_4=$ | 52.5 | 25.9 | 39.9 |
| $C_5=$ | 61.8 | 34.0 | 57.1 |
| $C_5$ Olefin Distribution, wt % | | | |
| $C_5=1$ | 1.5 | 1.3 | 2.0 |
| $2M1C_4=$ | 14.9 | 13.4 | 16.9 |
| $3M1C_4=$ | 1.0 | 1.0 | 1.3 |
| $T2C_5=$ | 11.3 | 12.4 | 12.1 |
| $C_2C_5=$ | 5.3 | 5.5 | 6.0 |
| $2M2C_4=$ | 66.1 | 66.4 | 61.6 |
| $C_6+$ Aromatics, wt % | 6.3 | 15.0 | 8.7 |
| Liq. Prod. 90% Pt., °F. (D-2887) | 408 | 380 | 373 |
| Conditioned in 1:1 $CO/H_2$, °F./hr | 609/17 | 610/17 | 610/17 |

| EXAMPLE | 15 | 16 | 18 |
|---|---|---|---|
| Run Time, Hours | 18 | 20.8 | 18 |
| GHSV | 541 | 1042 | 688 |
| WHSV | 0.99 | 1.01 | 0.99 |
| Temp., °F., Average | 558 | 548 | 548 |
| Hot Spot | 568 | 564 | 568 |
| CO Conversion, wt % | 53.0 | 60.7 | 61.9 |
| $H_2$ Conversion, wt % | 50.1 | 59.7 | 64.0 |
| % wt C Converted to: | | | |
| Hydrocarbon | 56.0 | 62.0 | 64.4 |
| Product Yield, wt % | | | |
| HC | 13.4 | 17.3 | 19.2 |
| $H_2O$ | 5.5 | 9.6 | 10.7 |
| $H_2$ | 3.6 | 2.8 | 2.6 |
| CO | 43.6 | 36.6 | 35.4 |
| $CO_2$ | 34.0 | 33.7 | 32.2 |
| Hydrocarbon Composition, wt % | | | |
| $C_1$ | 30.8 | 15.7 | 18.1 |
| $C_2$ | 22.1 | 10.1 | 9.3 |
| $C_3$ | 6.9 | 15.8 | 8.4 |
| $C_4$ | 10.3 | 12.0 | 9.9 |
| $C_5$ | 5.2 | 10.7 | 10.7 |
| $C_6+$ | 24.8 | 35.8 | 43.6 |
| Olefins, wt % by C No. | | | |
| $C_2=$ | 8.8 | 28.0 | 38.8 |
| $C_3=$ | ~0 | 74.6 | 64.2 |
| $C_4=$ | 26.6 | 77.2 | 78.6 |
| $C_5=$ | 37.4 | 78.0 | 84.2 |
| $C_5$ Olefin Distribution, wt % | | | |
| $C_5=1$ | 1.2 | 26.9 | 3.4 |
| $2M1C_4=$ | 14.8 | 4.3 | 14.6 |
| $3M1C_4=$ | 0.8 | 3.1 | 1.2 |
| $T2C_5=$ | 11.3 | 35.8 | 19.6 |
| $C_2C_5=$ | 5.1 | 21.5 | 9.6 |
| $2M2C_4=$ | 66.8 | 8.5 | 51.5 |
| $C_6+$ Aromatics, wt % | 7.3 | 0.2 | 0.4 |
| Liq. Prod. 90% Pt., °F. (D-2887) | 391 | 448 | 383 |
| Conditioned in 1:1 $CO/H_2$, °F./hr | 612/17 | 604/16 | 613/15 |

| EXAMPLE | 19 | 20 | 21 |
|---|---|---|---|
| Run Time, Hours | 20.5 | 40.5 | 18 |
| GHSV | 680 | 997 | 891 |
| WHSV | 0.98 | 1.02 | 1.01 |
| Temp., °F., Average | 548 | 539 | 562 |
| Hot Spot | 574 | 568 | 568 |
| CO Conversion, wt % | 81.7 | 92.0 | 27.3 |
| $H_2$ Conversion, wt % | 69.6 | 75.1 | 36.4 |
| % wt C Converted to: | | | |
| Hydrocarbon | 57.3 | 57.5 | 73.7 |
| Product Yield, wt % | | | |
| HC | 22.0 | 26.1 | 8.7 |
| $H_2O$ | 7.9 | 7.7 | 8.7 |
| $H_2$ | 2.1 | 1.8 | 4.5 |
| CO | 17.1 | 7.4 | 67.6 |
| $CO_2$ | 50.9 | 57.1 | 10.5 |
| Hydrocarbon Composition, wt % | | | |
| $C_1$ | 18.2 | 16.5 | 22.2 |
| $C_2$ | 10.6 | 7.9 | 7.5 |
| $C_3$ | 16.0 | 4.5 | 6.6 |
| $C_4$ | 11.7 | 7.4 | 16.6 |
| $C_5$ | 9.9 | 11.4 | 8.2 |
| $C_6+$ | 33.7 | 52.4 | 38.9 |
| Olefins, wt % by C No. | | | |
| $C_2=$ | 22.0 | 9.3 | 28.0 |
| $C_3=$ | 65.6 | 14.8 | ~0 |

| -continued | | | |
|---|---|---|---|
| $C_4=$ | 78.9 | 46.0 | 11.2 |
| $C_5=$ | 78.5 | 62.3 | 13.2 |
| $C_5$ Olefin Distribution, wt % | | | |
| $C_5=1$ | 18.6 | 1.9 | 1.1 |
| $2M1C_4=$ | 3.8 | 17.4 | 14.9 |
| $3M1C_4=$ | 4.1 | 1.5 | ~0 |
| $T2C_5=$ | 39.5 | 11.5 | 13.8 |
| $C_2C_5=$ | 21.6 | 5.7 | 6.4 |
| $2M2C_4=$ | 12.4 | 62.0 | 63.8 |
| $C_6+$ Aromatics, wt % | 0.2 | 1.3 | 18.4 |
| Liq. Prod. 90% Pt., °F. (D-2887) | 477 | 379 | 358 |
| Conditioned in 1:1 $CO/H_2$, °F./hr | 612/64.5 | 605/64 | 610/22 |

| EXAMPLE | 22 | 23 | 24 |
|---|---|---|---|
| Run Time, Hours | 18 | 18 | 18 |
| GHSV | 821 | 831 | 788 |
| WHSV | 0.96 | 0.99 | 1.06 |
| Temp., °F., Average | 553 | 552 | 554 |
| Hot Spot | 566 | 570 | 570 |
| CO Conversion, wt % | 25.2 | 87.3 | 58.2 |
| $H_2$ Conversion, wt % | 51.5 | 70.3 | 50.7 |
| % wt C Converted to: | | | |
| Hydrocarbon | 86.2 | 56.1 | 62.3 |
| Product Yield, wt % | | | |
| HC | 10.2 | 23.5 | 16.4 |
| $H_2O$ | 12.0 | 6.9 | 9.1 |
| $H_2$ | 3.9 | 2.3 | 3.3 |
| CO | 68.9 | 11.7 | 39.0 |
| $CO_2$ | 5.0 | 55.6 | 32.2 |
| Hydrocarbon Composition, wt % | | | |
| $C_1$ | 15.3 | 17.9 | 20.7 |
| $C_2$ | 5.5 | 6.8 | 6.5 |
| $C_3$ | 4.1 | 5.5 | 5.7 |
| $C_4$ | 11.7 | 10.0 | 12.0 |
| $C_5$ | 10.3 | 5.6 | 4.0 |
| $C_6+$ | 53.1 | 54.1 | 51.2 |
| Olefins, wt % by C No. | | | |
| $C_2=$ | 48.3 | 5.6 | 21.5 |
| $C_3=$ | 36.2 | 12.8 | ~0 |
| $C_4=$ | 41.8 | 13.4 | 5.1 |
| $C_5=$ | 55.8 | 17.6 | 6.3 |
| $C_5$ Olefin Distribution, wt % | | | |
| $C_5=1$ | 1.7 | 1.3 | ~0 |
| $2M1C_4=$ | 16.7 | 15.6 | 15.4 |
| $3M1C_4=$ | 1.2 | 0.9 | ~0 |
| $T2C_5=$ | 11.6 | 12.1 | 12.8 |
| $C_2C_5=$ | 5.8 | 5.6 | 5.1 |
| $2M2C_4=$ | 63.0 | 64.5 | 66.7 |
| $C_6+$ Aromatics, wt % | 11.1 | 19.2 | 33.8 |
| Liq. Prod. 90% Pt., °F. (D-2887) | 364 | 387 | 385 |
| Conditioned in 1:1 $CO/H_2$, °F./hr | 615/17 | 610/17 | 611/17 |

| EXAMPLE | 25 | 26 | 27 |
|---|---|---|---|
| Run Time, Hours | 18 | 18 | 18 |
| GHSV | 906 | 626 | 928 |
| WHSV | 0.97 | 0.98 | 1.06 |
| Temp., °F., Average | 548 | 557 | 559 |
| Hot Spot | 566 | 567 | 574 |
| CO Conversion, wt % | 75.2 | 33.4 | 43.6 |
| $H_2$ Conversion, wt % | 65.8 | 45.8 | 48.2 |
| % wt C Converted to: | | | |
| Hydrocarbon | 59.4 | 74.3 | |
| Product Yield, wt % | | | |
| HC | 21.9 | 11.3 | 15.1 |
| $H_2O$ | 8.5 | 9.4 | 12.7 |
| $H_2$ | 2.7 | 3.8 | 3.4 |
| CO | 22.9 | 61.9 | 52.7 |
| $CO_2$ | 44.1 | 13.6 | 16.2 |
| Hydrocarbon Composition, wt % | | | |
| $C_1$ | 18.2 | 19.7 | 13.4 |
| $C_2$ | 12.1 | 9.3 | 5.6 |
| $C_3$ | 6.5 | 3.6 | 3.7 |
| $C_4$ | 8.5 | 11.6 | 18.8 |
| $C_5$ | 9.6 | 8.7 | 13.9 |
| $C_6+$ | 45.1 | 47.1 | 44.7 |
| Olefins, wt % by C No. | | | |
| $C_2=$ | 7.5 | 21.4 | |
| $C_3=$ | 21.1 | 36.1 | |
| $C_4=$ | 47.2 | 27.9 | |
| $C_5=$ | 60.8 | 29.1 | |
| $C_5$ Olefin Distribution, wt % | | | |
| $C_5=1$ | 2.0 | 1.4 | |
| $2M1C_4=$ | 17.4 | 15.8 | |
| $3M1C_4=$ | 1.5 | 1.1 | |
| $T2C_5=$ | 12.1 | 11.6 | |
| $C_2C_5=$ | 6.0 | 5.6 | |
| $2M2C_4=$ | 61.1 | 64.6 | |
| $C_6+$ Aromatics, wt % | 4.4 | 12.0 | 13.6 |
| Liq. Prod. 90% Pt., °F. (D-2887) | 370 | 371 | 378 |
| Conditioned in 1:1 $CO/H_2$, °F./hr | 600/17 | 600/15 | 612/17 |

The data presented in the above table vividly demonstrates the superiority of the catalyst prepared in accordance with the instant invention.

Thus, Example 2 is a catalyst prepared in accordance with the instant invention using ferr*ous* oxalate. Example 7a and 7b use the water soluble compound ferr*ic* oxalate. Note that Example 2 yielded 64.9 wt % $C_5+$ whereas Example 7a gave 33.6 wt % and Example 7b gave 55.4 wt %.

Note that the in situ formation of ferrous oxalate resulted in more active catalysts than adding ferrous oxalate directly. Compare Examples 2 and 4 wherein it can be seen that the in situ preparation (Example 4) was more active in that it converted 83.9 wt % CO as opposed to 51.4 wt % and yielded more hydrocarbons, i.e 23.4 wt % as opposed to 16.4 wt %.

Note that the catalyst of Example 23 gave better results than the impregnated catalyst of Example 27, i.e. CO conversion of 87.3 wt % as opposed to 43.6. Total hydrocarbons were 23.5 wt % versus only 15.1 wt %.

What is claimed:

1. A process for converting synthesis gas comprising carbon monoxide and hydrogen to a hydrocarbon product comprising at least 45 weight percent of $C_5+$ naptha while limiting the production of methane plus ethane to no more than 30 weight percent which comprises contacting said synthesis gas at a temperature of from about 500° to 600° F. and at a pressure of from 50–1000 psig with a catalyst containing from about 2.5 to 20 weight percent Fe prepared by forming a homogenous mixture of a water insoluble, decomposable iron derivative of an organic compound, a matrix, and an acidic crystalline aluminosilicate zeolite having a silica-to-alumina ratio of at least 12, a pore size greater than about 5 Angstrom units and a constraint index of about 1 to 12, drying and heating said mixture to decompose the organic iron compounds, and treating it with carbon monoxide or mixtures containing the same at elevated temperatures.

2. The process of claims 1, 3, 4, 5, or 6 wherein the catalyst contains from about 2.5 to 10 weight percent Fe.

3. The process of claim 1 wherein said catalyst has been spray dried to produce fluid size particles.

4. The process of claim 1, wherein said iron compound is ferrous oxalate.

5. The process of claim 3, wherein said iron compount is ferrous oxalate.

6. The process of claim 4, wherein said ferrous oxalate is formed in situ.

7. The process of claims 1, 3, 4, 5, or 6, wherein said treatment with carbon monoxide or mixtures containing the same is carried out at atmospheric pressure and at temperatures of about 550°–650° F. for periods of time ranging from about ½ hours up to about 24 hours.

8. The process of claim 1, wherein said matrix is prepared from colloidal dispensions of silica and alumina.

* * * * *

UNITED STATES PATENT AND TRADEMARK OFFICE
CERTIFICATE OF CORRECTION

PATENT NO. : 4,255,349
DATED : March 10, 1981
INVENTOR(S) : Stephen A. BUTTER and Arthur W. CHESTER It is certified that error appears in the above-identified patent and that said Letters Patent are hereby corrected as shown below:

Column 6, line 10, delete "and the" second occurrence

Column 11, line 9, insert --size-- after "particle"

Column 11, line 20, change "gel" to --sol--

Column 12, line 4, change "impregnating" to --impregnation--

Column 12, line 12, change "5.2" to --5.3--

Column 18, line 50, after "claim" delete "1,"

Column 18, lines 57/58, change "compount" to --compound--

Signed and Sealed this

Sixth Day of October 1981

[SEAL]

Attest:

GERALD J. MOSSINGHOFF

Attesting Officer

Commissioner of Patents and Trademarks